United States Patent [19]

Prahl

[11] 3,950,443
[45] Apr. 13, 1976

[54] UTILIZATION OF WASTE PRODUCTS CONTAINING CHLORINE IN THE PRODUCTION OF CHLORINATED ORGANIC COMPOUNDS BY COMBINATION OF OXYCHLORINATION WITH COMBUSTION

[76] Inventor: Walter H. Prahl, Pfaffstrasse 16, 75 Karlsruhe 41, Germany

[22] Filed: Sept. 27, 1973

[21] Appl. No.: 401,378

[52] U.S. Cl...... 260/650 R; 260/654 A; 260/656 R; 260/658 R; 260/659 A; 260/662 A
[51] Int. Cl.² ........................................ C07C 25/00
[58] Field of Search........ 260/659 A, 662 A, 654 A, 260/650 R, 656 R, 658 R

[56] References Cited
UNITED STATES PATENTS

| | | | |
|---|---|---|---|
| 1,963,761 | 6/1934 | Prahl | 260/650 R |
| 2,395,314 | 2/1946 | Blumer | 260/659 A |
| 3,234,295 | 2/1966 | Sprauer | 260/656 R |
| 3,363,010 | 1/1968 | Schwarzenbek | 260/659 A |
| 3,548,016 | 12/1970 | Sze | 260/659 R |

Primary Examiner—Delbert E. Gantz
Assistant Examiner—Joseph A. Boska
Attorney, Agent, or Firm—Sidney B. Ring; Hyman F. Glass

[57] ABSTRACT

Two byproducts of the chlorine-consuming industry, weak hydrochloric acid and chlorine-containing organic wastes, are utilized in the production of chlorinated organics, preferably hydrocarbons, by oxychlorination. The chlorine-containing organic waste is burned, liberating its chlorine content as HCl, its heat content being used to evaporate weak hydrochloric acid by direct contact with the combustion gases, and the mixture is passed, with organics, preferably hydrocarbons, and air, over an oxychlorination catalyst of the Deacon type. The chlorinated organic, preferably hydrocarbon, is recovered by conventional means.

3 Claims, 3 Drawing Figures

UTILIZATION OF WASTE PRODUCTS CONTAINING CHLORINE IN THE PRODUCTION OF CHLORINATED ORGANIC COMPOUNDS BY COMBINATION OF OXYCHLORINATION WITH COMBUSTION

Chlorination of organic materials, for instance in the production of solvents like trichloroethylene, plastics monomers like vinylchloride, intermediates of glycols, etc., and in many other branches of the chemical process industry, produces two Principal byproducts: Hydrogen chloride (HCl), and chlorine-containing organic waste products mostly of higher chlorine content, higher molecular weight or other undesired property (herein referred to as "Cl-waste").

Hydrogen chloride is formed in most chlorinations in quantities up to one half of the chlorine consumed. By the use of pressure, condensation, absorption in water, removal of impurities, etc., most of it is recovered in commercially useful form, that is an gaseous or liquified hydrogen chloride, or as concentrated hycrochloric acid. Part of it, however, is inevitably transformed to dilute hydrochloric acid. Owing to the azeotropic behaviour of the system HCl-water, HCl in commercially useful form cannot be recovered by simple distillation or other inexpensive procedures from dilute hydrochloric acid of less than about 20% HCl content. Hydrochloric acid of less than about 20% HCl is, therefore, also a waste product in the sense of this invention.

Disposal of these two waste products, dilute hydrochloric acid and Cl-waste, poses an ecological problem. Dilute hydrochloric acid is conventionally neutralized by lime, etc., and disposed of as a solution of $CaCl_2$ where that is ecologically feasible. Disposal of Cl-waste is more problematical. Its persistant, obnoxious and poisonous nature prevents dumping. Combustion liberates its chlorine content in form of HCl and $Cl_2$, two gases which are ecologically highly objectionable. Their dilution with large quantities of combustion gases, like nitrogen, carbon dioxide, and water, has heretofore prevented, their industrial use. In the conventional combustion of Cl-waste, therefore, both the chlorine content and the heat content are lost. In addition expensive provisions have to be made for the safe disposal of the combustion gases. One method is to release them into the atmosphere in places remote from habitation. Cl-waste is collected for instance in a ship equipped with tanks and burners, carried to a part of the ocean not frequented by ships, and there burned, where HCl and $Cl_2$ are intended to be absorbed by the ocean. The technical, economical, and ecological objections to such procedure are obvious. Other methods try to avoid $Cl_2$ and recover the HCl by absorption in water as dilute hydrochloric acid. (For instance: Chemical Engineering Progress, 69 (1973) Jan. p. 68 – 74.) Such methods are ecologically more acceptable because they do not discharge the HCl into the atmosphere, and they appear to be more economical because they recover the HCl. In practical terms, however, they just replace one waste product with another. The chlorine content of the Cl-waste is used to produce dilute hydrochloric acid, which in itself is a waste product particularly in those places where Cl-waste occurs. And the energy content of the Cl-waste is not used at all.

There exists therefore in the chlorine consuming industry the two problems of (a) disposing of Cl-waste in such a way that its energy content as well as its chlorine content is recovered in a commercially useful form, and (b) disposing of dilute hydrochloric acid in a commercially useful form.

Both problems are solved, simultaneously, according to the present invention, by the combination of combustion with oxychlorination.

Oxychlorination can be visualized as a modification of the Deacon process. The Deacon process converts HCl to $Cl_2$ according to the equation $4 HCl + O_2 \rightleftarrows 2 Cl_2 + 2 H_2O$ by passing a mixture of HCl and oxygen at elevated temperature over a catalyst conventionally containing copper. The practical usefulness of the Deacon process is limited by its equilibrium conditions. Only by using starting materials of the highest concentrations can reasonable concentrations of $Cl_2$ be obtained in the product mix. Particularly harmful is the presence of water. In oxychlorination an organic substance is added to the reaction mixture of the Deacon process. It acts as an acceptor of chlorine, lowering the concentration of $Cl_2$ in the equilirium and thereby facilitating the progress of the reaction.

Oxychlorination as a unit operation was introduced into the chemical process industry about forty years ago by the present inventor in the large scale production of chlorobenzene, according to the equation

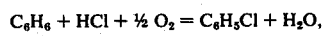
$C_6H_6 + HCl + ½ O_2 = C_6H_5Cl + H_2O,$ as part of the so called Raschig phenol process. (U.S. Pat. No. 1,963,761) Since then oxychlorination has been applied to the production of many other chlorinated compounds, including the chloromethanes, chloro-ethanes, and other aliphatic chlorine substitution products, dichloroethane produced on a very large scale by the addition of chlorine to ethylene, according to the equation

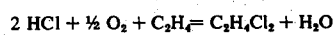
$2 HCl + ½ O_2 + C_2H_4 = C_2H_4Cl_2 + H_2O$ which is then cracked to vinyl chloride, including further the chlorination products of naphthalene, biphenyl, and other aromatics. Organic substances or compounds to be subjected to oxychlorination will be referred to herein as "Organics."

Oxychlorination is not as sensitive to the presence of water or to the dilution of the reaction mixture by other substances, as the Deacon process, but in principle the same considerations apply to it. The combustion gases of Cl-waste contain HCl in low concentration, diluted with large quantities of nitrogen, carbon dioxide, water, etc., and in the vapors of dilute hydrochloric acid the HCl is diluted by large quantities of water. Oxychlorination has never before been applied to HCl of anywhere near the dilution as in the present process, particularly not to HCl diluted by combustion gases, and it is obvious that oxychlorination in its conventional form would not be applicable. It is only owing to several unobvious and unexpected advantages appearing in, and achieved by, the combination of combustion and oxychlorination, that the process of the present invention becomes operable. Such advantages are, for instance, the ability to maintain an unconventionally, and unexpectedly high terminal HCl concentration, the ability to recycle the unreacted HCl without additional cost, the ability to vaporize the reactants by the heat of combustion alone, without additional heat, and many others. The following description will explain the advantages resulting from the combination of oxychlorination and combustion.

In order to demonstrate them, and in order to facilitate the understanding of the gist and scope of this invention, first, the operation of this invention will be explained in Example 1 as applied to the simple chlorination of benzene by Cl-waste alone. Then this example will be used to explain the gist of the invention and the advantages of employing the combination of combustion and oxychlorination. After that, several modifications of the invention will be illustrated in Examples 2 to 6, using for the sake of comparison, again the chlorination of benzene, and finally Example 7 to 9 will describe the chlorination of substances other than benzene.

EXAMPLE 1

This example demonstrates the recovery of the chlorine and the heat content of about 1,280 lbs/hour of a Cl-waste containing about 63.2% chlorine. It burns the Cl-waste and uses its chlorine content in the oxychlorination of benzene, producing mainly monochlorobenzene, together with some more highly chlorinated benzenes. Both are used industrially as solvents, intermediates, and for other purposes.

Figure 1:
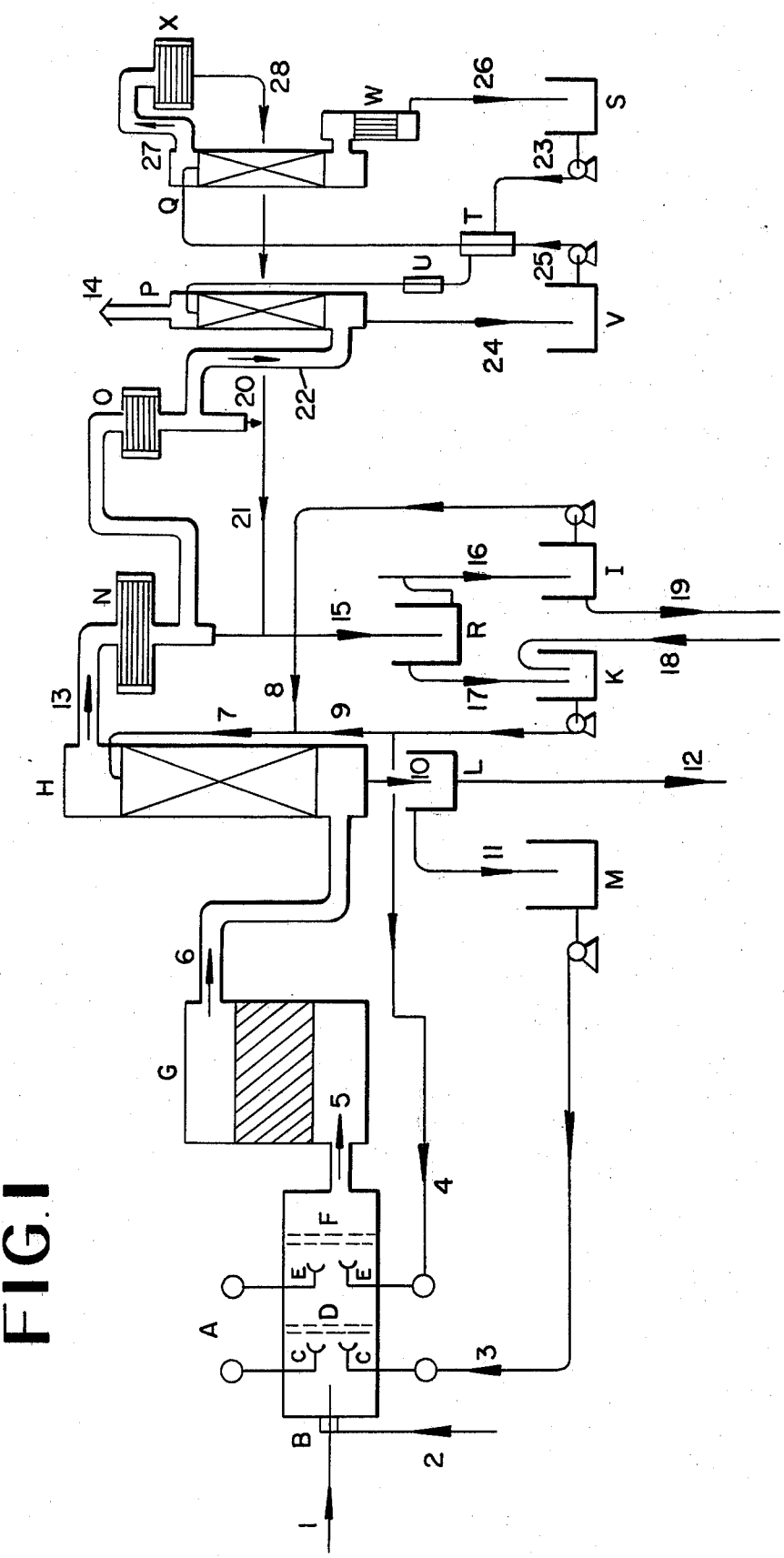
FIG. 1 shows schematically the equipment used in the process of Example 1.

The equipment used in Example 1 is shown schematically in FIG. 1. A represents a combustion chamber lined with refractory bricks, and equipped with burner B. About 1,280 lbs/h of Cl-waste is pumped through line 1 into burner B, ignited, and burned with about 7,590 lbs/h of air, blown through line 2 into the burner. C represents an arrangement of spray nozzles. About 2,916 lbs/h of about 2.85% hydrochloric acid are pumped through line 3 into the nozzles. The acid spray is evaporated by the hot combustion gases. A checkerwork of bricks D catches unevaporated drops, and protects the downstream portion of the equipment against the heat. Evaporation of the acid cools the combustion gases to about 600°C. E represents another arrangement of spray nozzles. Through them about 10,100 lbs/h of benzene from line 4 are sprayed into the gas stream. A checkerwork of bricks F serves to secure complete evaporation and mixing. The mixture leaving combustion chamber A through line 5 has now a temperature of about 200°C. It enters catalyst chamber G. Here it passes through about 700 cuft of a Deacon type catalyst, prepared for instance according to U.S. Pat. No. 1,963,761. About 90 % of the HCl entering G is consumed in the chlorination of benzene, forming about 2,075 lbs/h of mono-, 270 lbs/h of di-, 27 lbs/h of tri-chlorobenzene and a few lbs/h of higher chlorobenzenes. The reaction mixture passes through line 6 into the recovery system. In the preferred form for the present example the recovery system comprises a column H, being a bricklined steel cylinder of about 5 ft. internal diameter, and containing a packing of 2 inch saddles of porcelain about 20 ft. high. The packing is irrigated through line 7 with about 2,680 lbs/h of water coming through line 8 from water tank I, and about 26,700 lbs/h of benzene coming through line 9 from benzene tank K. The bottom discharge of column H passes through line 10 into separator L. Here it is separated into an aqueous phase containing essentially all the unreacted HCl and about 2,833 lbs/h of water. It passes through line 11 into acid tank M, and from there back through line 3 to combustion chamber A. The organic phase containing essentially all the chlorinated benzene and about 2,000 lbs/h of benzene, goes through line 12 to a conventional separation, for instance a fractional distillation, which separates it, for instance into benzene to return to the process, monochlorobenzene and the dichlorobenzenes for industrial use, etc. The top discharge of column H, consisting of about 1,600 lbs/h carbon dioxide, 3,280 lbs/h of water, 5,800 lbs/h of nitrogen, 70 lbs/h of oxygen, and 33,200 lbs/h of benzene goes first to condenser N, where it is cooled to about 30°C by means of recirculated water condensing most of the benzene, then to condensor O, where it is cooled by refrigerated water to about 15°C. The condensate flows via lines 20, 21, and 15 to separator R. The gas saturated with benzene and water at about 15°C passes through line 22 to a conventional absorption system. The gas flows upwards through column P. Its benzene content is absorbed by a suitable scrubbing liquor, in this case for instance orthodichlorobenzene, pumped from tank S through line 23, heat interchanger T and cooler U with about 10°C to the top of column P. The ortho-dichlorobenzene with the absorbed benzene leaves P through line 24 for equalizer tank V. From V it is pumped through line 25 and heat interchanger T to the top of stripping column Q. (If a slight recycle of dichlorobenzene is objectionable, line 25 would enter Q somewhat below the top, with some of the benzene from line 28 serving as reflux.) Q is preferably operated under a slight vacuum, for instance at 300 mm Hg abs. The dichlorobenzene is stripped of its absorbed benzene by passing down column Q in countercurrent to vapors of o-dichlorobenzene generated in reboiler W. The stripped dichlorobenzene flows through line 26 into tank S, and repeats the cycle. The benzene driven off in Q enters condenser X through line 27, and returns via lines 28, 21, and 15 into the system. The condensates of N, O, and X are carried through lines 28, 21, and 15, resp., into separator R which separates them into benzene and water. They return through lines 17 and 16, resp., to their tanks, the levels in the tanks are maintained by adding through line 18 about 1,625 lbs/h of benzene to K, and withdrawing about 400 lbs/h of water from I through line 19.

Conversion of the chlorine content of the Cl-waste is practically quantitative. The yield on the benzene, depending on operational factors, is in general higher than 95%.

Using now the specific operation of Example 1 as reference, in the following discussion the more general aspects, and the advantages of this invention over the prior practice, particularly over the operation of combustion and oxychlorination individually, will be discussed.

Combustion

In order to prevent corrosion of the equipment and to bring the catalyst to reaction temperature, the combustion is preferably started with a conventional fuel like gas or oil. After reaching the proper temperatures the burner is switched to Cl-waste. Depending upon circumstances, Cl-waste normally sustains combustion in special burners up to a chlorine content of about 65%. If the chlorine content is higher, or if owing to the design of the burner or for other reasons the combustion causes difficulties, the Cl-waste is diluted with a conventional fuel such as natural gas, fuel oil, etc. An important requirement is essential absence of sulfur. If either Cl-waste or fuel contain essential quantities of sulfur, special precautions have to be taken to prevent deterioration of the catalyst.

One of the advantages of the combination of combustion with oxychlorination becomes apparent in the combustion. Excess air in the combustion of Cl-waste favors formation of $Cl_2$ rather than HCl. In the conventional recovery of the chlorine content of Cl-waste in form of aqueous hydrochloric acid the presence of $Cl_2$ causes difficulties. The conventional method, therefore, has to strike a compromise between no excess of air with incomplete combustion, and the normal excess of air with the problems caused by the presence of $Cl_2$. In the combination of combustion with oxychlorination, this dilemna does not exist because in oxychlorination it makes no difference whether the Cl content is present as HCl or as $Cl_2$. They react with equal facility in the oxychlorination. In the process of the present invention the Cl-waste can therefore be burned with a comfortable excess of air. In example 1 this excess is selected so as to leave enough $O_2$ in the combustion gas to satisfy the $O_2$ requirement of the oxychlorination. If desired, however, a smaller excess of air can be used in the combustion, and the $O_2$ required in the oxychlorination can be added anywhere before or in the catalyst, in form of air, oxygen, or otherwise.

Quenching

The combustion gases leave the burner normally with a temperature considerably above 1000°C. Contact with the organic at this temperature would tend to destroy it. The next step is, therefore, to cool the combustion gases at least to a temperature tolerated by the organic without essential decomposition (in the following called "tolerance temperature"). For benzene under the given circumstances the tolerance temperature is about 600°C. For other organics and under other circumstances other tolerance temperatures would apply. The combustion gases must be cooled to, they may be cooled below, the tolerance temperature. In Example 1 they are cooled to the tolerance temperature only, in order to utilize the heat between tolerance and reaction temperature for the vaporization, and heating to reaction temperature of benzene. Where no vaporization is necessary, for instance where the organics are gases like methane, ethane, etc., the combustion gases can be cooled down to close to the reaction temperature, as shown in later examples.

Cooling of the combustion gases can be achieved by any of the conventional means. The preferred method is to cool them by evaporating dilute hydrochloric acid into them. The contact between hot combustion gas and quenching liquid can be effected, as in Example 1, by spraying the liquid into the gas stream. The temperature is then controlled by the quantity of liquid injected. Other methods of contact would be the use of submerged burners, a packing irrigated with the liquid, etc. Such methods would normally cool close to equilibrium temperature. Where a higher temperature, for instance tolerance temperature, is desired, splitting of the gas stream, with one cooled portion being mixed with an uncooled portion, or other means of temperature control may be necessary.

Heat Economy

The heat economy of the present process is governed by the following considerations:
Heat is generated
I. in the combustion, available
  a. from combustion temperature to tolerance temperature.
  b. from tolerance temperature to reaction temperature.
II. in the oxychlorination and by oxidation.
Heat is consumed
A. In evaporation, and heating to reaction temperature, of the unreacted HCl recovered as dilute hydrochloric acid.
B. In evaporation, and heating to reaction temperature, of any extra hydrochloric acid.
C. In evaporation in case of liquids, and/or heating to reaction temperature of the organic.

(Ia) cannot be used by the organic. This heat is to be used primarily for (A). Any unused portion is available for (B). (Ib) is to be used primarily for (C). Any unused portion can be used for (B). The distribution is governed by these considerations: The lower the ratio of HCl to organic, the higher is the ratio of lower to higher chloro-compounds. If in Example 1 preferentially mono-chlorobenzene is desired, all (Ib) and, where applicable, all of (II) is used to evaporate benzene, so as to react a minimum of HCl with a maximum of benzene. In the reverse case, and where for other reasons, as in the case of organic gases, the full amount of (Ib) is not used for C, the unused portion of (Ib) as well as (II) can be used for B.

Although the unreacted portion of HCl can theoretically be recovered as up to about 20% acid, it is normally more economical to recover it in lower concentration, say 10 to 15%. (In Example 1 it is recovered as only 2.85% acid, because for the sake of simplicity no extraneous HCl is added to that generated in the combustion.) On the other hand, an otherwise wasted quantity of stronger acid of, say, 20% may be available. It is not contrary to the spirit of this invention, in such cases to substitute the stronger acid, and discard, instead, the unreacted HCl. This is done, for instance, in Example 3.

Oxidation

The ability to recycle the unreacted HCl into the process represents a very important advantage for the oxychlorination. In order to explain it, one aspect of the oxychlorination reaction will be briefly discussed.

In every oxychlorination reaction the undesired oxidation of the organic, in case of benzene represented by the equation $C_6H_6 + 7½ O_2 = 6 CO_2 + 3H_2O$, competes for the oxygen with the desired oxychlorination, in this case $C_6H_6 + HCl + ½ O_2 = C_6H_5Cl + H_2O$. The relative rate of the two reactions depends upon many factors, such as the nature of the organic, properties of the catalyst, temperature, and others, but the most influential single factor is the concentration of HCl. Under otherwise equal circumstances oxidation increases rapidly with decreasing HCl concentration, apparently inversely proportional to the square or a higher power of the HCl concentration. In the conventional oxychlorination the utilization of HCl is therefore a compromise between losing unreacted HCl recovered as less than worthless weak acid, or losing organic oxidized owing to low terminal concentration of HCl. The conventional oxychlorination of benzene, for instance, leaves at least 2% of the HCl unreacted in order to keep the oxidation of benzene within limits. Conventional oxychlorination cannot be applied to many sensitive organics, for instance substituted benzenes, because their sensitivity to oxidation would require to keep the utilization of the HCl at intolerably low levels.

In the case of the present invention, however, this limitation does not exist. All unreacted HCl returns as quench liquor into the reaction, and the conversion of HCl is 100%, regardless whether each passage leaves 2 or 20 or 50 percent of the HCl unreacted. For the effect of the quenching liquid it makes no difference whether it is water or the equivalent quantity of hydrochloric acid.

Combustion of Cl-waste produces HCl at much lower concentrations than required in the conventional oxychlorination. In order to prevent excessive oxidation the terminal concentration of HCl has to be kept at a level analogous to that of the conventional oxychlorination. The conversion of HCl per passage is, therefore, necessarily lower. This could make the application of oxychlorination to the combustion gases of Cl-waste uneconomical, if it were not for the feature that very high percentages of the HCl can be recycled without additional expense, since the combustion gases have to be quenched anyway. In Example 1 the unreacted HCl is about 10% of the HCl entering the catalyst, that is about five times as high as in a conventional oxychlorination of benzene, and the percentage of benzene oxidized is kept at a minimum thereby. In the oxychlorination of organics more sensitive to oxidation than benzene, the percentage of unreacted HCl could be as high as 50 or more percent without sacrificing the economy of the process.

The ability to operate with low conversions of HCl per pass has another economic advantage. The quantity of catalyst required to convert a given quantity of HCl in a given time is an inverse function of the concentration of the HCl. A terminal concentration, say, five times as high compensates for the initial concentration being, say, five times as low as in conventional oxychlorination. The catalyst volume is thus roughly the same as in conventional oxychlorination. It seems that the ability of this process to recycle economically a very high percentage of unreacted HCl, with the consequences of low oxidation, practically 100% conversion of HCl, and conventional catalyst volume, in spite of low initial HCl concentration, is one of the more important features of this invention, making possible the application of oxychlorination to combustion gases.

Injection of the organic

The organic has to contact the catalyst as vapor or gas. Where it is initially a liquid, it is advantageous to use the difference between tolerance temperature, in case of benzene about 600°C, and reaction temperature, for benzene about 200°C, for the vaporization of the organic. In Example 1 liquid benzene is sprayed into the partly quenched combustion gas in a quantity controlled to lower its temperature from about 600°C to 200°C. The same effect could have been achieved by passing the gases through a layer of packing irrigated with benzene, or in any other conventional method of contacting gas and liquid. It should be noted that here, again, the heat of combustion is usefully employed. As the higher temperatures are used for vaporizing hydrochloric acid, so the lower ones are used for vaporizing the organic.

Catalyst Chamber

Both, oxychlorination and oxidation, reactions are exothermic. In conventional oxychlorination the reactor is cooled in order to prevent the reaction mixture from reaching a temperature at which oxidation prevails, and in order to prevent the formation of "hot spots," areas of the catalyst where in a vicious circle the temperature has risen, promoting oxidation, which in turn causes further rise in temperature, etc.

The cooling can be effected by external or internal means. Externally the tubes or plates containing the stationary catalyst are cooled by air, high boiling liquids, etc., or the fluidized catalyst is passed through a cooling zone. Internal cooling is effected by dividing the catalyst body into several beds connected in series, and injecting as cooling medium into the process stream between them one or more of the reactants in liquid or vapor phase, or an indifferent coolant. A liquid cooling medium can be, for instance, water, the liquid organic, hydrochloric acid, etc. A cooling medium in vapor phase can be, for instance, the gaseous organic, part of the cooled reaction mixture, nitrogen, etc. In any case the cooling requirement contributes to the cost and technical complication of an oxychlorination. In the process of the present invention the larger total mass for a given reacting mass causes a lower temperature rise for a given quantity of heat, the lower concentration of oxygen, organic and HCl minimizes the danger of hot spots, and the higher terminal concentration of HCl makes the mixture less sensitive to oxidation by higher temperatures. For these reasons, the reactor in the present invention requires in many cases no, in any case less and simpler, cooling than in the corresponding conventional oxychlorination. In a conventional oxychlorination of benzene, for instance, the temperature would rise by as much as 300°C or more, if no cooling were applied. In Example 1 the actual temperature rise is about 140°C. For a conventional oxychlorination such rise would be excessive. Under the conditions of Example 1 it is still permissible. The low concentration of oxygen and particularly the high terminal concentration of HCl prevent excessive oxidation. It is true, though, that the yield would be even better, if a divided catalyst bed, as for instance in FIG. 2, were used.

Catalyst

In principle, any Deacon type catalyst of high activity can be used. Copper hydroxide precipitated on highly active aluminum hydroxide, as described for example in my U.S. Pat. No. 1,963,761, is probably one of the best all-round catalysts. In the oxychlorination of ethane, and particularly for the production of ethylene dichloride, presence of rare earths seems to offer advantages. (Brit. Pat. Nos. 932,130; 907,435.) In order to prevent volatilization of copper, addition of alkali metals is recommended. A very extensive patent literature recommends modifications of the Deacon type catalyst for many special purposes, any or all of which may be useful in the implementation of this invention. Most of them, however, seem primarily aimed at lower oxidation and at lower terminal HCl concentration, a goal of minor importance to the process of the invention.

Column

The relatively large mass of gases and vapors issuing from the reactor at elevated temperature carries a considerable amount of heat. This heat is preferably used for a preliminary separation of the products by means of a countercurrent device such as a column. Owing to the low vapor pressure of HCl over dilute hydrochloric acid it is in most cases possible and advisable to recover practically all of the unreacted HCl in the bottom discharge of the column. Concentrations of 10 to 15% or higher are normally obtainable without having more than traces of HCl pass overhead.

Normally the chlorinated organic has a lower vapor pressure than the organic. In many cases it is therefore possible to recover most or all of the chlorination product in the bottom discharge of the column in good concentration, as in Example 1. In principle the isolation and recovery of the products of the present process is not different from that of the conventional oxychlorination.

Condensation

The same is true for the further treatment of the top discharge of the column. The vapors are condensed, preferably in several steps using progressively colder cooling media. Any organic or chlorinated organic remaining in the gas phase after condensation are recovered by conventional means, such as further cooling, absorption in scrubbing liquids, adsorption on charcoal, etc. Example 1 uses, as means suitable in the oxychlorination of benzene, cooling and condensation of the bulk of benzene to about 30°C by recirculated water, then cooling to about 15°C with refrigerated water, followed by absorption in ortho-dichlorobenzene. O-dichlorobenzene is one of the less desirable products of the oxychlorination of benzene, and its use as a scrubbing liquid may be one of its more advantageous uses.

Driving Force

The pressure differential required to move the mixture through the system is generated in the conventional manner by a pressure blower or similar device for the combustion air, or by a suction blower at or near the discharge of the gases into the atmosphere.

Example 2

Organic: Benzene. Source of HCl: Cl-waste with 81% Cl plus 20% hydrochloric acid. Source of heat: Cl-waste plus oil. Coolant: Benzene.

In Example 1 all the HCl and all the heat originated in the combustion of Cl-waste. The quench heat from tolerance to reaction temperature is used only for evaporation of unreacted HCl, and the heat generated in the reactor (reaction heat) is not used at all, except by aiding in the fractionation. Example 2, otherwise following closely the conditions of Example 1 in order to permit comparison, demonstrates the use of the quench heat for vaporizing hydrochloric acid as additional source of HCl, and of the reaction heat for vaporizing benzene as additional source of organic. The increased load in this case would result in too high a temperature rise in the catalyst. The reactor requires cooling. Internal cooling by evaporating a liquid between divided catalyst beds is the preferred method, although any of the other conventional methods of temperature control in catalytic reactions would be applicable. The choice for cooling liquid is here obviously either waste hydrochloric acid or benzene. The latter is preferred because (1) the ratio benzene/HCl is thus improved, and (2) elimination of water in the column is facilitated.

Figure 2:
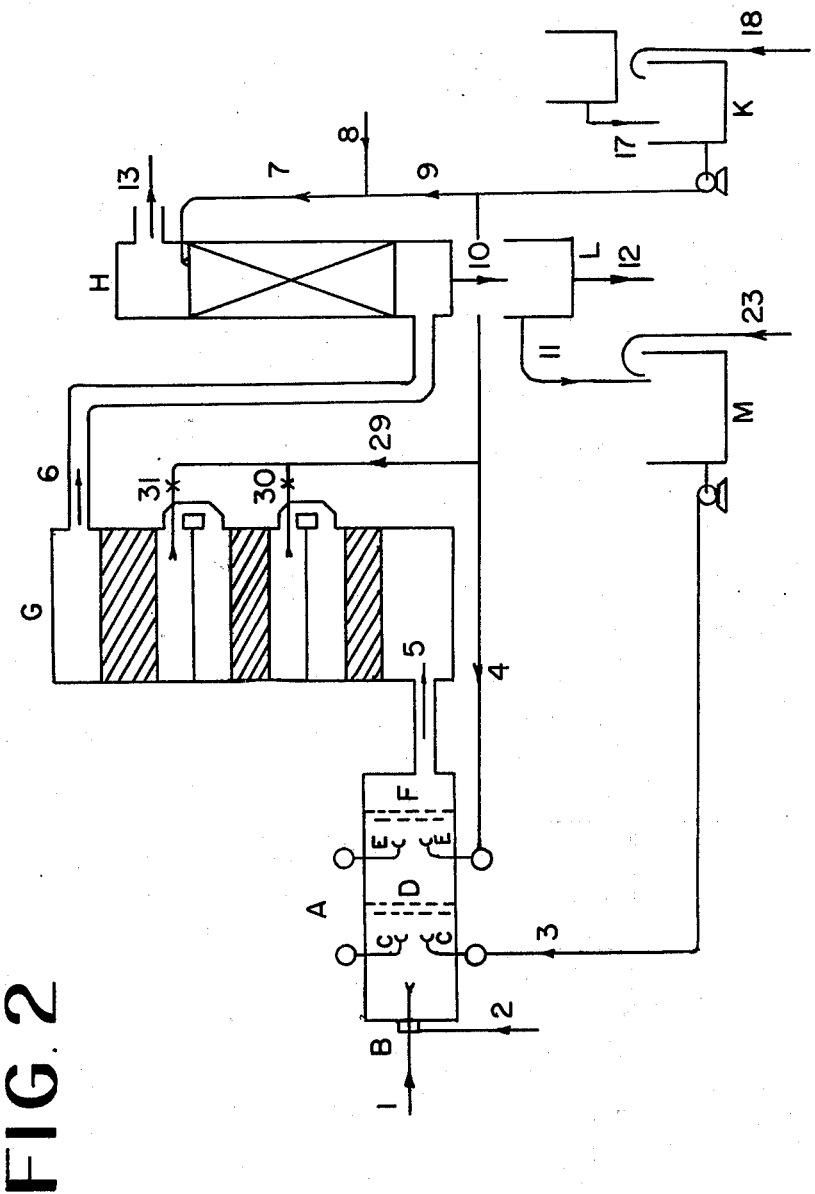
FIG. 2 shows the reactor portion of the equipment used in the process of Example 2.

The reactor portion of the equipment suitable for this case is shown schematically in FIG. 2, in which symbols, letters, and numbers have the same meaning as in FIG. 1. All quantities are in lbs/h, and all data are understood to be approximate.

1000 Cl-waste are mixed with 280 fuel oil, pumped to burner B and burned with 9400 air. 1627 hydrochloric acid with 20% HCl are added to acid tank M through line 23. The quench liquor carried through line 3 to spray nozzles C consists of 475 HCl and 2,152 water. Through line 4 and nozzles E 11,000 benzene are added, lowering the temperature to 200°C. The mixture passing through line 5 into reactor G consists then of 1,308 HCl, 1,563 $CO_2$, 2,340 $H_2O$, 7,250 $N_2$, 880 $O_2$, and 11,000 benzene. The reactor contains three beds of Deacon type catalyst, which the mixture passes in series. The depth of the beds is about 2 ft., 3 ft., and 5 ft., respectively. Controlled by valves 30 and 31, 7,300 benzene is injected into the reaction mixture between the beds, so as to reduce the inlet temperature into the 2nd and 3rd catalyst beds to about 200°C. The reacted mixture leaving the reactor through line 6 consists of 150 HCl, 1,660 $CO_2$, 2,930 $H_2O$, 7,250 $N_2$, 285 $O_2$, 16,000 $C_6H_6$ and 3,400 chlorinated benzenes of about the same composition as in Example 1. Column H separates the mixture into 150 HCl, 850 $H_2O$, 2,000 $C_6H_6$, and 3,400 chlorobenzenes, passing as bottoms through line 10 into separator L, from which the aqueous portion is recycled through line 11, acid tank M, and line 3 to the combustion chamber, while the organic phase passes through line 12 into the distillation, etc. About 2,350 benzene is added to tank K through line 18. The irrigation of column H consists of 20,500 benzene and 1,300 water.

The design of reactor G aims to maintain an equal temperature rise, in this case of about 60°C, in each catalyst bed. The proper reaction rate for that purpose is maintained in each bed by adjusting its inlet temperature. Depending on age of catalyst, thickness of bed, and many other factors it could be found, for instance, that the first bed, in order to have a temperature rise of, say, 60°C, requires an inlet temperature of, say, 190°C. The quantity of benzene through line 4 is then controlled so as to maintain this temperature in line 5. The second bed, in order to show a temperature rise of 60°C, may require an inlet temperature of, say 215°C. This temperature is maintained by the control of valve 30. The third bed may require an inlet temperature of 200°C, controlled by the quantity of benzene through 31.

EXAMPLE 3

Organic: Benzene. Source of HCl: Waste hydrochloric acid 15.5%. Source of heat: Natural gas. Coolant: Benzene. Unreacted HCl: rejected.

In Example 1 all the HCl originated in the Cl-waste. In Example 2 the excess heat of the combustion was used to evaporate hydrochloric acid as additional source of HCl. In Example 3 extraneous hydrochloric acid is the sole source of HCl.

Using the technique of this invention the heat for evaporating hydrochloric acid does not necessarily have to come from combustion of Cl-waste. According to this invention, hydrochloric acid can be evaporated into any other hot combustion gas generated by combustion of, for instance, fuel oil, natural gas, coke, etc. Technically this procedure offers no particular difficulties. Economically the advantages over the conventional evaporation of HCl by means of steam would not seem to be as large as when combustion of Cl-waste is the source of heat. There may be circumstances, however, in which this procedure is economical, for instance when operation is to be maintained during times of lack of Cl-waste, in the start-up or shut-down of the operation according to Examples 1 and 2, where equipment and/or steam for evaporating hydrochloric acid is too expensive, etc.

Example 3 represents also a case in which, owing to the introduction of large quantities of water into the reaction by the combustion of natural gas and by the use of dilute hydrochloric acid, it is advantageous to discard, rather than recycle, the unreacted HCl, in order to use all available heat for evaporation of waste acid stronger than the recovered unreacted HCl could be.

In the equipment of FIG. 2 750 natural gas containing 68% by weight methane, 29% ethane and 3% nitrogen is burned with 14,650 air. 7,100 hydrochloric acid 15.5% are evaporated into the combustion gases, bringing their temperature down to 600°C. 17,500 benzene is added through line 4. The mixture entering the catalyst chamber consists of 17,500 benzene, 1,100 HCl, 2,036 $CO_2$, 7,537 $H_2O$, 11,250 $N_2$ and 560 $O_2$. The temperature is controlled as explained in Example 2 by injecting 5,570 benzene between the beds. 100 unreacted HCl and 3,485 water is drawn off through line 11 and discarded, because here, where the fuel is burned just for its heat content, it is more economical to use the heat for evaporating 15.5%, than 2.8% hydrochloric acid. The product, drawn off the bottom of H contains 2,900 chlorobenzenes of a composition similar to that of the previous examples. The quantity of benzene consumed in the reaction is about 1,965. The yield based on the hydrochloric acid is in this case, of course, lower, about 91%.

EXAMPLE 4

Organic: Benzene. Source of HCl: Waste hydrochloric acid 18%. Source of heat: Coke. Coolant: Benzene. Unreacted HCl: Recycled.

Combustion of coke contributes little water to the reaction and, therefore, permits recycle of the unreacted HCl. 1,000 coke is burned on a chain grate, instead of burner B in FIG. 2, with 15,800 air. 6,582 18% hydrochloric acid is added to tank M. This quantity mixed with 1,538 13% hydrochloric acid containing the unreacted HCl condensed in H and passed to M via lines 10 and 11, is sprayed via line 3 and spray nozzles C into the combustion gases, cooling them to 600°C. About 15,500 benzene from tank K are sprayed via line 4 and spray nozzles C into the mixture, lowering its temperature to 200°C. In passing the catalyst chamber the mixture is cooled by injecting through lines and valves 29, 30, and 31 about 5,880 benzene, controlling the temperature as explained in Example 2. The reacted mixture is worked up in the conventional way. From 2,400 benzene and 6,582 18% hydrochloric acid, 3,440 chlorinated benzene of approximately the composition of Example 1 are obtained. The yield based on the hydrochloric acid is almost 100%, and based on the benzene over 95%.

Selectivity in chlorinating organics

In the foregoing I have described the combination of combustion with oxychlorination using benzene as the organic. I have pointed out, that in addition to the main advantage of recovering the chlorine content of waste products in commercially useful form, the combination results in a number of other advantages which could be designated as: Combustion with a comfortable amount of excess air, full use of the HCl, lower oxidation, simpler reactor design, applicability to oxygen-sensitive compounds, no requirement for extraneous heat, etc. In the following another advantage of the combination will be discussed, namely: Selectivity.

Oxychlorination is a reaction of low selectivity. Almost any and all of the theoretically possible chlorination stages and isomers are formed in almost any oxychlorination, and the means of steering a conventional oxychlorination are practically limited to controlling the ratio of organic to HCl. Consequently almost any conventional oxychlorination produces a mixture of compounds many of which may be undesirable byproducts. Taking again the oxychlorination of benzene as an example, it is possible to obtain mono-chlorobenzene as the main product by exposing a large quantity of benzene to a small quantity of HCl and $O_2$, maintaining a ratio of 10 or 20 to 1, but even then substantial quantities of mainly di- and some higher chlorobenzenes are formed as byproducts. To obtain, however, intermediate chlorination stages, such as for instance para-dichlorobenzene, exclusively, as the product of a conventional oxychlorination is impossible. (Para-dichlorobenzene is extensively used as crystals for moth protection.) Even in the most favorable case there would be more byproducts than main product.

The combination of combustion, however, with oxychlorination according to the present invention permits the exclusive production of any desired single compound or group of compounds. This is achieved by treating any byproducts of equal or higher chlorine content as Cl-waste in the sense of this invention, and recycling any byproducts of lower chlorine content as organic in the sense of this invention. This principle will be explained and demonstrated in Examples 5 and 6.

EXAMPLE 5

Exclusive production of mono-chlorobenzene

Organic: Benzene. Source of HCl: Cl-waste 81% Cl. Source of Heat: Cl-waste and oil. Coolant: None. Unreacted HCl: Recycled.

This example serves to illustrate one way of proceeding where the compound of the lowest chlorination stage is desired as the only product. The procedure is explained by describing the conversion of 1,000 Cl-waste into 2,570 mono-chlorobenzene.

Figure 3:
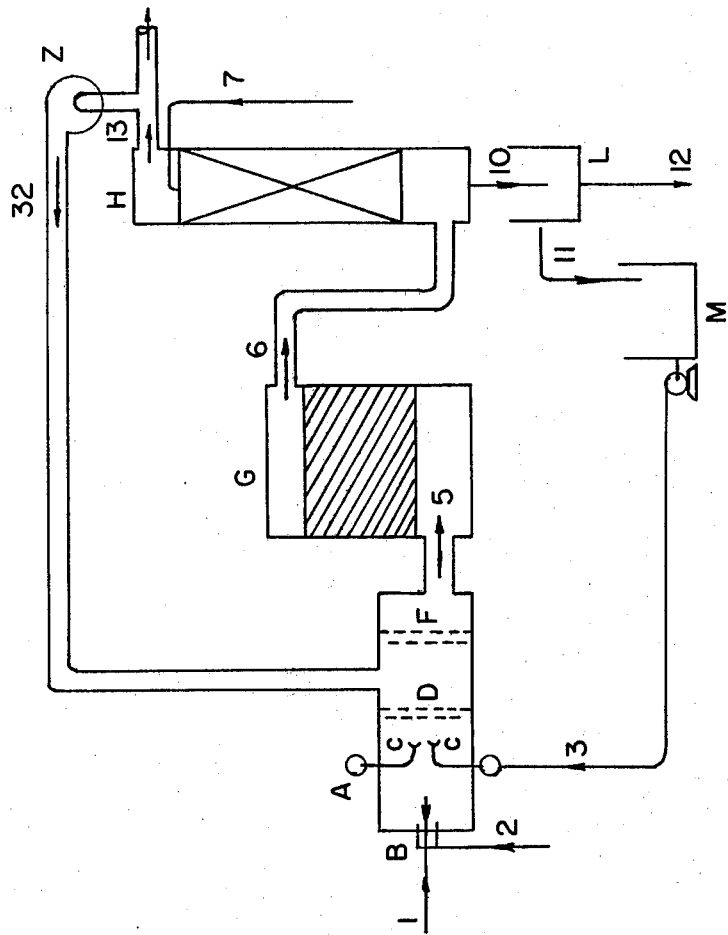
FIG. 3 shows the reaction part of the equipment suitable for use in the process of Example 5.

In order to obtain in the reaction a maximum percentage of the lowest chlorination stage, the ratio organic/HCl should be maximized. In order to maximize, in relation to the available heat, the quantity of benzene going into the reaction, the benzene is preferably introduced in vapor form, preferably by recycling part of the top discharge of the column. FIG. 3 is a schematic representation of the reaction part of equipment suitable for that purpose. Symbols, letters, and numbers have the same meaning as in FIG. 1, and 2.

1,000 Cl-waste of Example 2 are mixed with the residue of the distillation separating the mono-chlorobenzene from the more highly chlorinated benzenes. This residue consists essentially of 157 di-, and 13 tri-chlorobenzene. In order to bring the chlorine content of the mixture down to about 65% 204 fuel oil is added. The mixture is pumped through line 1 into burner B. 7,930 air is passed through line 2 into the burner. The combustion gases are cooled to 600°C by spraying through spray nozzles C 3,466 hydrochloric acid of about 2.9% into them. This acid is the aqueous portion of the bottom discharge of column H, which has been separated in L, passed through 11 into M, and is pumped through 3 into C. It contains 100 unreacted HCl and 3,366 water.

Approximately one half of the top discharge of column H leaving through line 13 is passed through blower Z and line 32 into the second compartment of the combustion chamber, and is mixed there with the combustion gases cooled to 600°C, lowering their temperature to 200°C. The composition of the gas-vapor mixture entering reactor G is then: HCl 1,018, $CO_2$ 3,220, $H_2O$ 6,515, $N_2$ 12,083, $O_2$ 665, benzene 30,647. The reaction consumes about 1892 benzene and forms about 2,570 mono-, 157 di-, and 13 tri-chlorobenzene, with negligible quantities of higher chlorobenzenes. The catalyzed reaction mixture leaves reactor H through line 6 with about 265°C and enters column H. The irrigation of column H through line 7 with about 3,040 water and 40,540 benzene is adjusted so that essentially all unreacted HCl and chlorinated product together with about 2,000 benzene leaves the bottom, while essentially all gases and the benzene-water azeotrope form the top discharge. The latter is treated in the conventional way, for instance as described in Example 1 to recover the benzene. The organic phase of the bottom discharge is separated in the conventional way, preferably by fractional distillation, into benzene which returns into the process via tank K, monochlorobenzene, and distillation residue. The latter is mixed with the Cl-waste and oil, as described at the beginning of this example, and burned. In this example 1,000 Cl-waste and 1,892 benzene yield about 2,570 mono-chlorobenzene. The yield based on benzene is about 94%, that on HCl about 100%. No byproducts are formed.

EXAMPLE 6

Exclusive production of para-dichlorobenzene.

Organic: Benzene. Source of HCl: Hydrochloric acid 18%. Source of heat: Cl-waste. Coolant: None. Unreacted HCl: Recycled.

This example demonstrates the production of exclusively para-dichlorobenzene in the oxychlorination of benzene according to the present invention. Para-dichlorobenzene, being used as moth crystals, is probably the most valuable chlorination product of benzene. It is unlikely, however, that none of the byproducts could be used more economically than by combustion. In this respect, this example in this form may be economically unrealistic. It serves to show, however, the technical feasibility of such exclusive production, leaving it to the economic circumstances to decide, how far in any given case this technique can be applied for the greatest economy. In this example the quantity of recycled Cl-waste is so high, and its chlorine content so low that considerably more heat is generated in the combustion than required for evaporating the unreacted HCl. This excess heat is available to evaporate dilute hydrochloric acid and use it as the sole source of chlorine.

In equipment represented by FIG. 1 a mixture of about 333 ortho-dichlorobenzene, 100 trichlorobenzenes, and 110 higher chlorobenzenes is burned with about 4,342 air. 1,380 hydrochloric acid from an extraneous source are added to tank M. Together with 50 unreacted HCl in 487 water they are pumped from M through 3 to spray nozzles C, quenching the combustion gases to about 600°C. 2,600 benzene and 7,000 mono-chlorobenzene from tank K through line 4 are injected through spray nozzles E. In evaporating, they cool the mixture to 200°C. Passing through reactor G increases the temperature to about 275°C. This temperature rise is entirely acceptable under the circumstances, no cooling is necessary, and the reactor is again a simple steel tank. The catalyzed mixture leaving G through line 6 consists of 50 HCl, 927 $CO_2$, 1,929 water, 3,330 $N_2$, 60 $O_2$, 2,060 benzene, 7,000 mono-chlorobenzene, 500 para-dichlorobenzene, 333 ortho-dichlorobenzene, a little meta-chlorobenzene, 100 tri-chlorobenzenes, and 110 tetra-, penta-, and hexa-chlorobenzenes. Column H separates the mixture in the conventional way into a bottom product containing 50 unreacted HCl, 487 water, 1,000 mono-chlorobenzene, and essentially all the higher chlorobenzenes. The organic phase is separated in L and worked up in the conventional way. For instance, a fractional distillation gives as the first fraction monochlorobenzene with a little benzene. It is recycled to tank K. The second fraction contains the dichlorobenzenes. This fraction is separated by cooling and crystallizing into the desired para-dichlorobenzene crystals, and the mother liquor containing some para-, and the ortho- and meta-dichlorobenzene. The para-dichlorobenzene is recovered from the mother liquor by distillation. The distillation residues are recycled to burner B as described in the beginning of this example. In this example 1,380 hydrochloric acid of 18% and 540 benzene are converted to 500 para-dichlorobenzene crystals, with no byproducts besides water and carbon dioxide. The yield based on HCl is almost quantitative, that on benzene only about 50%. As explained above, this example is therefore to be considered for its technical, rather than economical, recommendation.

Oxychlorination of substances other than benzene

In the preceding text the gist of the invention to combine combustion with oxychlorination has been explained, several methods of implementing it have been described, and the advantages of the combination over the individual operations have been demonstrated, all by using the oxychlorination of benzene as an example.

In the following the application of this invention to the oxychlorination of substances other than benzene will be described. Equipment and operation of the simplest type, analogous to FIG. 1 and Example 1 will be used. It will be obvious to those skilled in the art to apply the modifications of process and equipment shown in FIGS. 2 and 3 and in Examples 2 to 6, any combination of their features and other alterations, to the basic type of oxychlorination of naphthalene, natural gas, and ethylene, shown in Examples 7 to 9, as well as to that of any other substance to which oxychlorination is actually or potentially applicable.

EXAMPLE 7

In the equipment of FIG. 1 1,280 Cl-waste like that of Example 1 is burned with 8,000 air. 83 unreacted HCl in 3,360 water is injected through line 3. (Obviously, a large excess of heat is here available, which can be used for evaporating extraneous hydrochloric acid, if a higher chlorination of naphthalene is desired, or which can replace part of the Cl-waste as source of HCl.) About 12,000 molten naphthalene are injected through 4, bringing the temperature to about 230°C. In the reaction 2,800 naphthalene are converted to about 3,000 α-chloronaphthalene, 340 β-chloronaphthalene, 190 di-chloronaphthalenes, and 25 more highly chlorinated naphthalenes. Column H separates the mixture into about 83 HCl and 3,360 water recycled through 11, M, and 3, and the organic phase consisting of 7,700 naphthalene and 3,555 chlorinated product passing through 12 to the separation preferably by distillation. The overhead leaving the column through 13 consists of about 1,650 $CO_2$, 8,550 $H_2O$, 6,140 $N_2$, 115 $O_2$, and 1,430 naphthalene. Most of the latter is recovered by cooling to just above the melting point of naphthalene. The rest is recovered according to the conventional methods of the tar products industry. Column H is irrigated with about 7,900 water, preferably the condensate of the column overhead, and 2,000 naphthalene. The yield based on HCl is almost quantitative, that on naphthalene more than 95%.

EXAMPLE 8

Oxychlorination of natural gas

Source of HCl: Hydrochloric acid 15%. Source of heat: Natural gas. Coolant: Hydrochloric acid. Unreacted HCl: Used as coolant.

In equipment similar to that represented schematically in FIG. 2 100 natural gas containing about 68% by weight methane, 29% ethane and 3% nitrogen is burned in burner B with 2,500 air. The combustion gases are cooled to about 250°C by injecting 1,346 15% hydrochloric acid through nozzles C. 200 natural gas are added through line 4 and a suitable gas mixing device instead of spray nozzles. The mixture is passed at a starting temperature of about 240°C through the three catalyst beds of G. On its way from the first to the second, and from the second to the third the mixture heated by the reaction is brought back to about 240°C by injecting through 29, 30, and 31 a total of 500 hydrochloric acid 10%. Column H is irrigated with water so that the unreacted HCl of about 50 is absorbed in 450 water. This acid is used for cooling between the catalyst beds. The overhead of column H contains the product in form of various chlorinated methane and ethane derivatives and their hydrolysis products, as in the conventional oxychlorination of methane, ethane, or their mixtures. Their recovery follows the conventional methods.

EXAMPLE 9

Production of 1,2-Dichloroethane

Organic: Ethylene. Source of HCl: PVC-scrap, 15% hydrochloric acid. Source of heat: PVC-scrap. Coolant: 16% hydrochloric acid. Unreacted HCl: Recycled.

Symmetrical dichloroethane is an important intermediate in the production of vinylchloride. Large quantities are produced by oxychlorination of mainly ethylene, and some ethane. Large quantities of polyvinylchloride in form of sheets, bottles and other plastic products are discarded as waste or scrap, and burned. The HCl and $Cl_2$ content of the combustion gases poses severe ecological problems. The present invention solves them by using the chlorine and heat content of PVC-scrap to produce the intermediate in the production of PVC.

It is, of course, entirely feasible to use the heat of combustion of the PVC-scrap exclusively for the evaporation of unreacted HCl, and use its chlorine content as the sole source of HCl. Its heat content, however, is large enough to permit its economical utilization for the evaporation of additional quantities of waste hydrochloric acid. This example shows the use of 500 PVC-scrap. Its chlorine content supplies 292 HCl. Its heat content evaporates 360 HCl consisting of 100 unreacted HCl recycled in form of 10% hydrochloric acid, and 260 HCl added in form of 15% waste acid. About two-thirds of the heat of oxychlorination and oxidation are used to evaporate another 250 HCl injected in form of 16% hydrochloric acid as coolant into the process stream between the catalyst beds. The chlorine and heat content of 500 PVC-scrap is thus utilized to convert 802 HCl into 1,063 chloro-ethanes.

The process is carried out in equipment of FIG. 2. 500 PVC-scrap, molten or powdered, is burned with 4,050 air. The gases are quenched to about 235°C by injecting 360 HCl and 2,373 water through spray nozzles C. Through a gas distributing device instead of nozzles E 350 ethylene are mixed into the stream. The mixture entering the reactor, then, consists of 625 HCl, 704 $CO_2$, 2,517 $H_2O$, 3,110 $N_2$, 300 $O_2$, and 350 $C_2H_4$. The inlet temperature into the three catalyst beds is controlled so that each bed has an approximately equal temperature rise of about 60°C. The inlet temperature into bed one is controlled by the quantity of hydrochloric acid into the combustion chamber through 3, that of the second bed by controlling the quantity of hydrochloric acid through 30, that of the third bed by controlling the hydrochloric acid through 31. The reaction mixture enters column H through line 6. The column is used in this case for the fractionation of hydrochloric acid only. Essentially all the product is in the top discharge through line 13, and goes to a conventional condensing and recovery system. The column is irrigated with about 2,000 water recirculated from the condensing system, and controlled so as to recover essentially all of the 100 unreacted HCl in form of about 10% hydrochloric acid. Yield on the HCl is practically 100%, of the 350 ethylene about 61 is lost with the off gas. The 1,063 product contains about 82% sym. dichloroethane, 14% trichloroethane, and 4% higher chloroethanes.

I claim:

1. A process of preparing chlorinated hydrocarbons by the oxychlorination process which comprises:
   1. Oxidizing combustible chlorine-containing hydrocarbon waste material to form a combustion gas,
   2. mixing the combustion gas with a hydrocarbon, a chlorinated hydrocarbon or mixtures thereof,
   3. contacting said mixture in the vapor phase with an oxychlorination catalyst, and
   4. recovering the chlorinated hydrocarbon obtained in the process.

2. Process of claim 1 in which the chlorine-containing combustible waste material is the only source of hydrogen chloride consumed in the oxychlorination.

3. Process of claim 1 in which part of the hydrochloric acid is derived from hydrochloric acid evaporated into the hot combustion gas.

* * * * *